(12) United States Patent
Grosso

(10) Patent No.: US 6,525,230 B2
(45) Date of Patent: Feb. 25, 2003

(54) ZONE REACTOR

(75) Inventor: Philip Grosso, Auburn, CA (US)

(73) Assignee: GRT, Inc., The Woodlands, TX (US)

( * ) Notice: Subject to any disclaimer, the term of this patent is extended or adjusted under 35 U.S.C. 154(b) by 0 days.

(21) Appl. No.: 10/114,579

(22) Filed: Apr. 2, 2002

(65) Prior Publication Data

US 2002/0156328 A1 Oct. 24, 2002

Related U.S. Application Data

(63) Continuation-in-part of application No. 09/951,570, filed on Sep. 11, 2001, now Pat. No. 6,462,243.
(60) Provisional application No. 60/284,642, filed on Apr. 18, 2001.

(51) Int. Cl.⁷ .................. C07C 27/00; C07C 29/00; C07C 41/00; C07C 27/10; C07C 27/12; C07C 27/14; C07C 27/16
(52) U.S. Cl. .................. 568/891; 568/671; 568/893; 568/894; 568/910
(58) Field of Search .................. 568/671, 891, 568/893, 894, 910

(56) References Cited

U.S. PATENT DOCUMENTS

| | | | | |
|---|---|---|---|---|
| 3,172,915 A | * | 3/1965 | Borkowski et al. | 260/614 |
| 3,310,380 A | * | 3/1967 | Lester | 23/216 |
| 5,243,098 A | * | 9/1993 | Miller et al. | 568/893 |
| 5,334,777 A | * | 8/1994 | Miller et al. | 568/859 |
| 5,998,679 A | * | 12/1999 | Miller | 568/859 |

\* cited by examiner

Primary Examiner—Johann Richter
Assistant Examiner—Elvis O. Price
(74) Attorney, Agent, or Firm—Michael A. O'Neil

(57) ABSTRACT

In a method of converting alkanes to their corresponding alcohols and ethers a vessel comprises a hollow, unsegregated interior defined first, second, and third zones. In a first embodiment of the invention oxygen reacts with metal bromide in the first zone to provide bromine; bromine reacts with the alkane in the second zone to form alkyl bromide; and the alkyl bromide reacts with metal oxide in the third zone to form the corresponding alcohol and/or ether. Metal bromide from the third zone is transported through the vessel to the first zone and metal oxide from the first zone is recycled to the third zone. A second embodiment of the invention differs from the first embodiment in that metal oxide is transported through the vessel from the first zone to the third zone and metal bromide is recycled from the third zone to the first zone. In a third embodiment of the invention the flow of gases through the vessel is reversed to convert the metal oxide back to metal bromide and to convert the metal bromide back to the metal oxide.

3 Claims, 3 Drawing Sheets

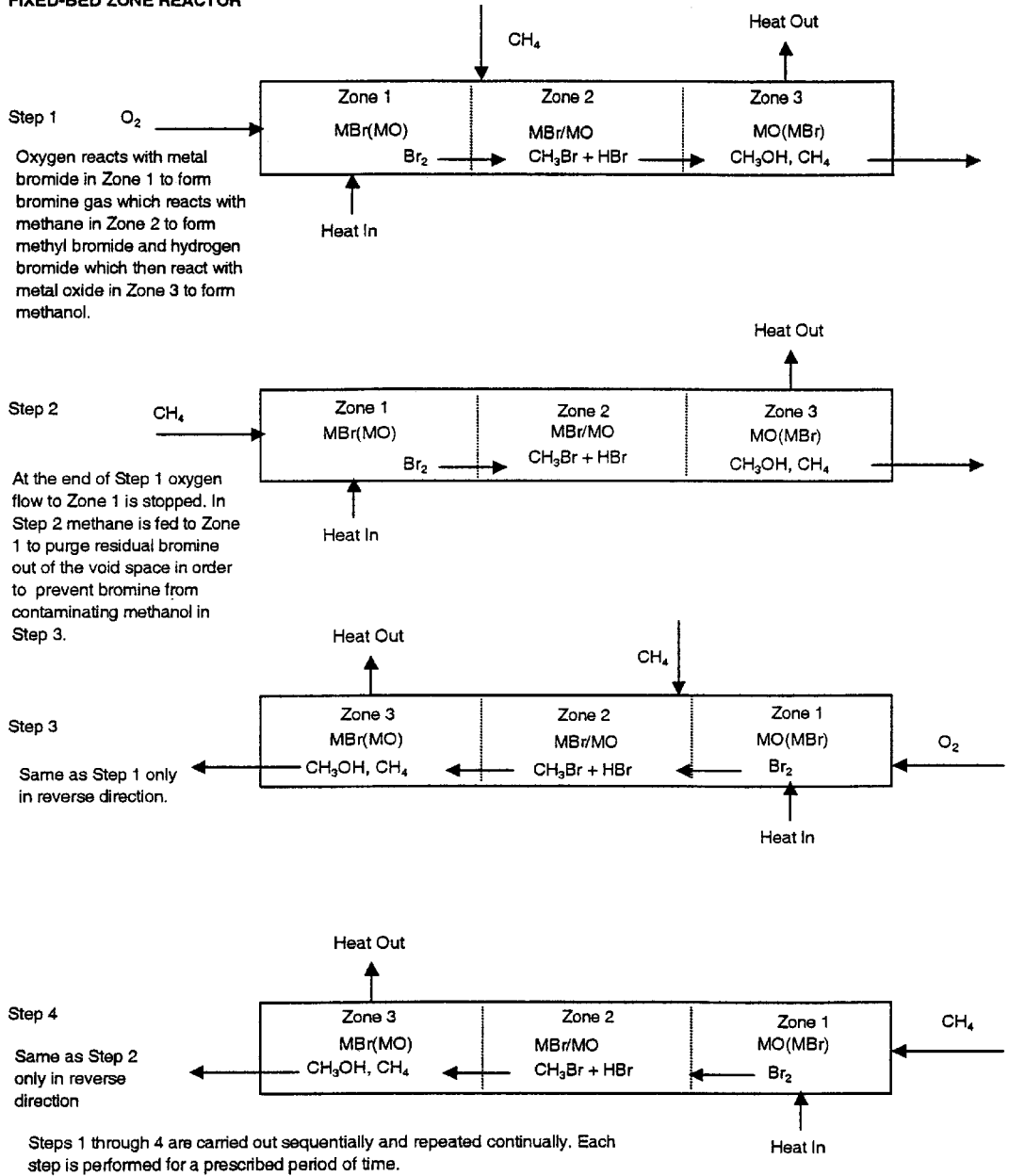

ZONE REACTOR

CROSS-REFERENCE TO RELATED APPLICATIONS

This is a continuation-in-part application under 37 C.F.R. §1.63 of application Ser. No. 09/951,570 filed Sep. 11, 2001, now U.S. Pat. No. 6,462,243; and provisional application Ser. No. 60/284,642 filed Apr. 18, 2001.

TECHNICAL FIELD

This invention relates to a zone reactor, and more particularly to a zone reactor that is useful in processes for converting alkanes to alcohols and ethers.

BACKGROUND AND SUMMARY OF THE INVENTION

Allowed co-pending application Ser. No. 09/951,570 filed Sep. 11, 2001 (Attorney Docket 300100-1044) discloses a method of converting alkanes to their corresponding alcohols and ethers using bromine. The co-pending parent application comprises four embodiments of the invention therein disclosed each including a reactor wherein bromine reacts with an alkane to form alkyl bromide and hydrogen bromide, a converter wherein the alkyl bromide formed in the reactor reacts with metal oxide to form the corresponding alcohol or ether, and numerous other individual components.

The present invention comprises a zone reactor wherein the several reactions disclosed in the co-pending parent application are carried out in a single vessel. In this manner the overall complexity of the system for converting alkanes to their corresponding alcohols and ethers is substantially reduced. In addition, heat generated by reactions occurring in particular zones within the vessel can be utilized to facilitate reactions occurring in other zones.

Three embodiments of the invention are disclosed. In accordance with a first embodiment the zone reactor comprises a countercurrent system wherein gases flow in a first direction and metal compounds flow in the opposite direction. A second embodiment of the invention comprises a cocurrent arrangement wherein the gases and the metal compounds travel in the same direction. The first and second embodiments of the invention are continuous systems as opposed to the third embodiment of the invention which is a fixed-bed system that is continual in operation. In accordance with the third embodiment the metal compounds remain fixed within the vessel while the gases are directed through the vessel first in one direction and later in the opposite direction.

In the following Detailed Description the invention is described in conjunction with the conversion of methane to methanol. However, as will be appreciated by those skilled in the art, the invention is equally applicable to the conversion of ethane and the higher alkane to their corresponding alcohols and ethers.

BRIEF DESCRIPTION OF THE DRAWINGS

A more complete understanding of the present invention may be had by reference to the following Detailed Description when taken in connection with the accompanying Drawings wherein:

FIG. 3 is a diagrammatic illustration of a fixed bed zone reactor comprising a third embodiment of the invention.

DETAILED DESCRIPTION OF THE INVENTION

Figure 1:
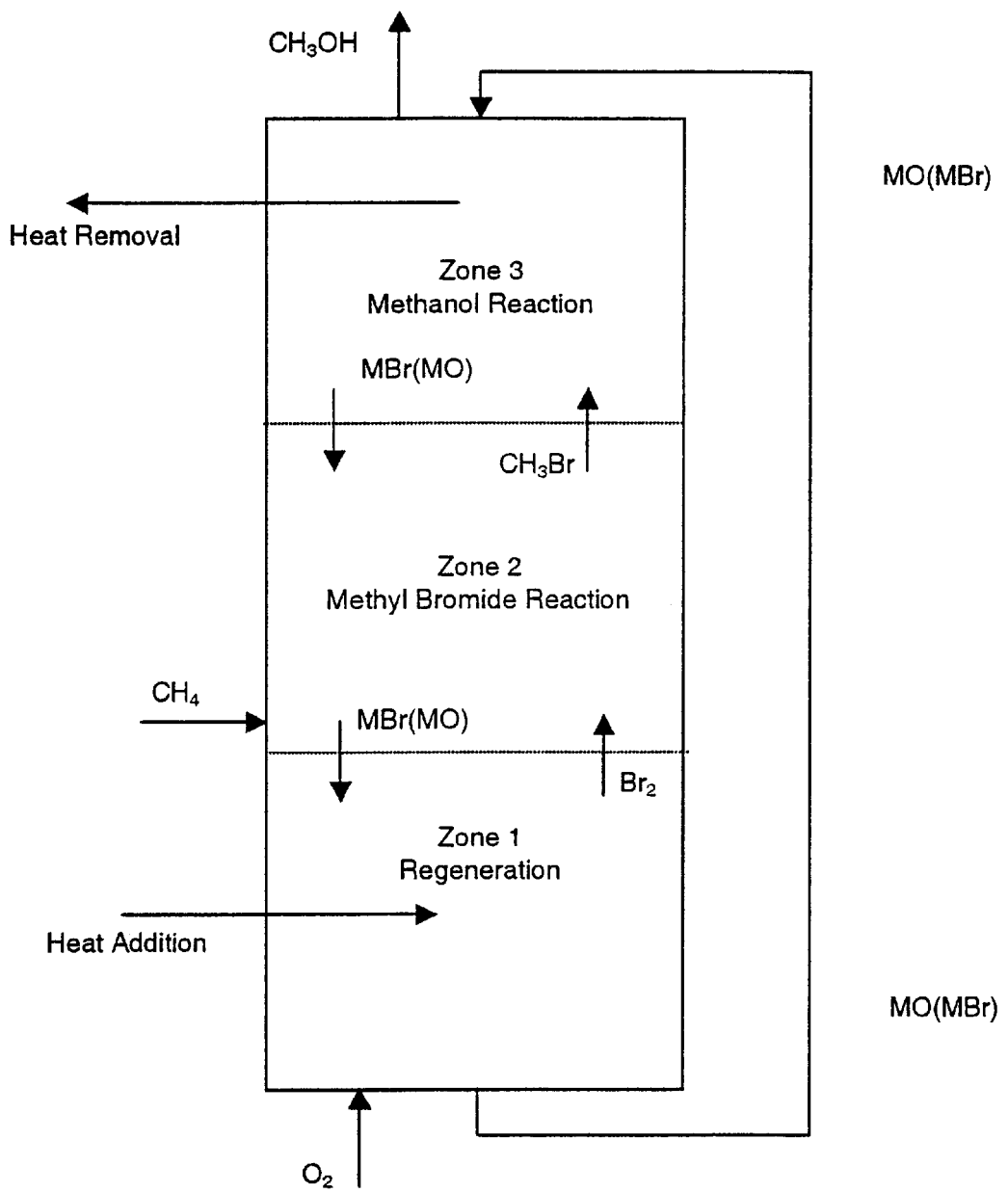
FIG. 1 is a diagrammatic illustration of a countercurrent zone reactor comprising a first embodiment of the invention.

The present invention comprises a zone reactor wherein three sequential chemical reactions occur in separate zones within a single vessel. In Zone 1 oxygen is reacted with a metal bromide to form bromine gas and the corresponding metal oxide. Bromine gas from Zone 1 passes to Zone 2 where the second chemical reaction occurs. In Zone 2 methane gas is introduced at an intermediate point in the vessel. Methane reacts with the bromine from Zone 1 to form methyl bromide and hydrogen bromide. The latter gasses pass into Zone 3 where the third chemical reaction causes methyl bromide and hydrogen bromide to react with metal oxide to form methanol and metal bromide. Methanol is converted to the liquid phase by condensation and is recovered from the reactor vessel as a liquid. Excess gasses, mostly methane, are separated from the recovered methanol and are returned to the zone reactor along with fresh methane. Metal oxide from Zone 1 is transported to Zone 3 where it proceeds from Zone 3 through Zone 2 to Zone 1 thereby completing the cycle.

Reactions in Zone 1 are endothermic; therefore, means to supply heat are provided. Zone 2 and Zone 3 involve exothermic reactions therefore, means to remove heat are provided.

The separation of zones is not necessarily a sharp one since there is no physical barrier between zones. Therefore, some overlap of reactions may occur. The important element, however, is that all the oxygen is converted to metal oxide in Zone 1 so that little or no oxygen remains to react with methane in Zone 2. In Zone 2 other bromides, i.e., higher brominated species, in addition to methyl bromide may form and result in products other than methanol in Zone 3, such as various ethers. Any by-products are separated from methanol in various isolation/purification steps. Any unreacted methane in Zone 2 will pass through Zone 3 and be recycled in Zone 2. Other unreacted brominated species are returned to Zone 2 either for reaction or to suppress further formation of the higher brominated species by satisfying the chemical equilibrium.

The zone reactor operates at essentially atmospheric pressure and at temperatures up to about 750F. The principal advantage over conventional methanol process lies in the simplicity of the system. The zone reactor achieves the synthesis of methanol in a single vessel whereas the conventional process requires multiple vessels to first produce synthesis gas followed by catalytic reaction. Furthermore the zone reactor operates at slightly above atmospheric pressure whereas the conventional process requires pressures up to 200 atmospheres.

As will be appreciated by those skilled in the art, the zone reactor of the present invention can be used with ethane and higher alkanes to produce corresponding alcohols and ethers.

The zone reactor also has advantages over a multi-step process utilizing the same bromine chemistry. One advantage is that one step replaces several. In addition, bromine gas remains in one vessel and need not be condensed and re-vaporized.

As will be appreciated by those skilled in the art, the zone reactor of the present invention can be used with ethane and higher alkanes to produce corresponding alcohols and ethers.

FIG. 1 shows a countercurrent system employing the zone reactor of the present invention. In this embodiment gasses flow upward through a bed of solids which is moving downward. Oxygen is introduced at the bottom of the vessel and reacts with a metal bromide to form bromine gas and the corresponding metal oxide. This step entails regeneration of the metal oxide, which was expended in Zone 3. Bromine from Zone 1 proceeds to Zone 2 where methane gas is introduced. The methane reacts with the bromine to form methyl bromide and hydrogen bromide. The latter two gasses proceed upward to Zone 3 where fresh metal oxide reacts with these gasses to form methanol and metal bromide. The regenerated metal oxide from Zone 1 is returned to Zone 3 thereby completing the cycle.

The reaction in Zone 1 may require heat. If so, a suitable heat supply apparatus is provided. In Zone 2 the reactions are exothermic. Heat from the Zone 2 reactor is allowed to raise the temperature of the gasses formed. Zone 3 involves reactions that may require the removal of heat; therefore, a suitable heat removal apparatus is provided.

Figure 2:
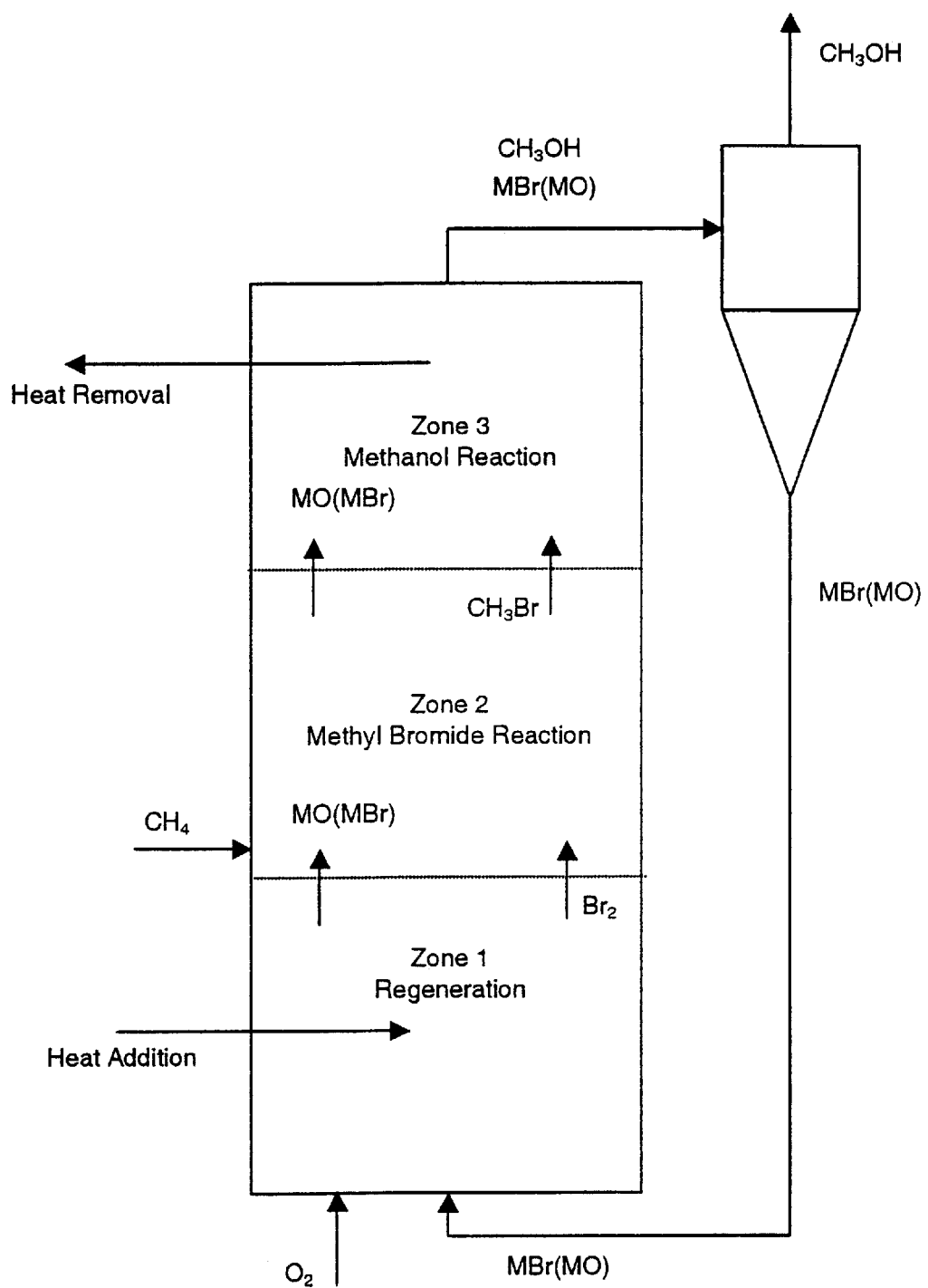
FIG. 2 is a diagrammatic illustration of a cocurrent zone reactor comprising a second embodiment of the invention.

FIG. 2 shows a cocurrent system employing the zone reactor concept. In this system gasses and solids proceed together in the same direction. In addition the solids are suspended in the gas flow in a way such that the gasses transport the solids. This embodiment combines the reaction steps with the physical movement of the solids. The chemical reaction steps are as described for FIG. 1.

FIG. 3 shows a fixed-bed system comprising a third embodiment of the invention. Whereas FIGS. 1 and 2 describe continuous systems, FIG. 3 describes a continual system. In the system of FIG. 3 the metal bromide/oxide solids remain fixed within the vessel while gasses are passed through the vessel. The regeneration step is carried out in place by reversing the flow of gases through the system. The steps involved and the order in which they are performed are described in FIG. 3. This mode of operation distinguishes itself by avoiding movement of solids as in the embodiments of FIGS. 1 and 2. In addition, by carefully setting the duration of each step the heat generated in Zones 2 and 3 can be at least partially allowed to raise the temperature of the bed. Then, when flow is reversed and Zone 3 becomes Zone 1, the heat stored in the solids can be used to provide the reaction heat needed in Zone 1. In this way the overall effect is a direct transfer of heat from the exothermic zone to the zone where it is needed without going through an intermediate step such as steam generation. However, since the heat generated in Zones 2 and 3 is likely to be greater than that needed in Zone 1, it may still be necessary to remove some heat from the system.

The physical separation of the chemical species formed is accomplished by conventional means, with valuable products and by-products recovered and other useful species returned to the appropriate zone for conversion or satisfaction of chemical equilibrium.

Although preferred embodiments of the invention have been illustrated in the accompanying Drawing and described in the foregoing Detailed Description, it will be understood that the invention is not limited to the embodiments disclosed but is capable of numerous rearrangements, modifications, and substitutions of parts and elements without departing from the spirit of the invention.

What is claimed is:

1. A method of converting alkanes to their corresponding alcohols and/or ethers comprising the steps of:

providing a vessel having an unsegregated hollow interior defining a first zone, a second zone, and a third zone;

reacting metal bromide and oxygen in the first zone of the vessel to form metal oxide and bromine;

reacting bromine from the first zone with alkane in the second zone of the vessel to form alkyl promide;

reacting alkyl bromide from the second zone and metal oxide in the third zone of the vessel to form a reaction product selected from the group consisting of the alcohol and the ether corresponding to the alkyl bromide reactant and metal bromide;

transporting the metal bromide from the third zone of the vessel to the first zone thereof; and recycling metal oxide from the first zone of the vessel to the third zone thereof.

2. A method of converting alkanes to their corresponding alcohols and/or ethers comprising the steps of:

providing a vessel having an unsegregated hollow interior defining a first zone, a second zone, and a third zone;

reacting metal bromide and oxygen in the first zone of the vessel to form metal oxide and bromine;

reacting bromine from the first zone with alkane in the second zone of the vessel to form alkyl bromide;

reacting alkyl bromide from the second zone and metal oxide in the third zone of the vessel to form a reaction product selected from the group consisting of the alcohol and the ether corresponding to the alkyl bromide reactant and metal bromide;

transporting the metal oxide from the first zone of the vessel through the vessel to the third zone thereof; and recycling metal bromide from the third zone of the vessel to the first zone thereof.

3. A method of converting alkanes to their corresponding alcohols and/or ethers comprising the steps of:

providing a vessel having an unsegregated hollow interior defining a first zone, a second zone, and a third zone;

initially reacting metal bromide and oxygen in the first zone of the vessel to form metal oxide and bromine;

reacting bromine from the first zone with alkane in the second zone of the vessel to form alkyl bromide;

reacting alkyl bromide from the second zone and metal oxide in the third zone of the vessel to form a reaction product selected from the group consisting of the alcohol and the ether corresponding to the alkyl bromide reactant and metal bromide;

subsequently reversing the flow of gases within the vessel and thereafter:

reacting metal bromide and oxygen in the third zone of the vessel to form metal oxide and bromine;

reacting bromine from the third zone with alkane in the second zone of the vessel to form alkyl bromide;

reacting alkyl bromide from the second zone and metal oxide in the first zone of the vessel to form a reaction product selected from the group including the alcohol and the ether corresponding to the alkyl bromide reactant and metal bromide.

* * * * *